United States Patent
Kuhr et al.

[11] Patent Number: 5,958,215
[45] Date of Patent: Sep. 28, 1999

[54] DETECTION OF PURINE AND PYRIMIDINE NUCLEOTIDES AND UNDERIVATIZED NUCLEIC ACIDS BY SINUSOIDAL VOLTAMMETRY

[75] Inventors: Werner G. Kuhr, Hesperia; Pankaj Singhal, Riverside, both of Calif.

[73] Assignee: The Regents of the University of Califronia, Oakland, Calif.

[21] Appl. No.: 08/896,548

[22] Filed: Jul. 18, 1997

Related U.S. Application Data

[63] Continuation-in-part of application No. 08/529,661, Sep. 18, 1995, Pat. No. 5,650,061.

[51] Int. Cl.$^6$ .................................................... G01N 27/26
[52] U.S. Cl. .......................... 205/787; 205/775; 205/792; 204/400; 204/434
[58] Field of Search ................................. 204/400, 434; 205/787, 792, 775, 794

[56] References Cited

U.S. PATENT DOCUMENTS

| | | | |
|---|---|---|---|
| 4,589,958 | 5/1986 | Alexander et al. | 204/400 |
| 5,403,451 | 4/1995 | Riviello et al. | 204/434 |
| 5,650,061 | 7/1997 | Kuhr et al. | 204/434 |

OTHER PUBLICATIONS

Long et al, "Voltammetry in Static and Flowing Solutions with a Large–Amplitude Sine Wave Potential", *Electroanalysts*, vol. 4, (1992) month unavailable, pp. 429–437.

*Primary Examiner*—T. Tung
*Attorney, Agent, or Firm*—Daniel L. Dawes

[57] ABSTRACT

Sinusoidal voltammetry was employed to detect both purine and pyrimidine-based nucleic acids. Adenine and cytosine, representing these two classes of nucleic acids, could be detected with nanomolar detection limits at a copper electrode under these conditions, where the sensitivity for adenine was much higher than that for cytosine. Detection limits for purine-containing nucleotides (e.g., adenosine 5'-monophosphate (AMP), adenosine 5'-diphosphate (ADP), and adenosine 5'-triphosphate (ATP)) were on the order of 70–200 nM using this method. These detection limits are achieved for native nucleotides and are over two orders of magnitude lower than those found with UV absorbance detection. Pyrimidine-based nucleotides could also be detected with high sensitivity due to the presence of a sugar backbone which is electroactive at the copper surface. This detector is not fouled by the nucleotides and can be used for the sensitive detection of analyses eluting continuously from a chromatography column or a electrophoresis capillary. Entire nucleic acid molecules can be readily detected. For example, both single stranded and double stranded DNA is detected with a detection limit in the picomolar concentration range (i.e., $10^{-12}$ moles/L). In the present invention, the signal from a double stranded DNA is roughly twice that arising from a single stranded DNA strand of the same length.

24 Claims, 2 Drawing Sheets

DETECTION OF PURINE AND PYRIMIDINE NUCLEOTIDES AND UNDERIVATIZED NUCLEIC ACIDS BY SINUSOIDAL VOLTAMMETRY

The present application is a Continuation In Part of application Ser. No. 08/529,661, filed Sep. 18, 1995 and issued as U.S. Pat. No. 5,650,061 on Jul. 22, 1997.

This invention was made with United States Government support under Grant No. CHE-8957394, awarded by the Nation Science Foundation and Grant No. GM 44112-01-08, awarded by the National Institute of Health. The Government has certain rights in this invention.

BACKGROUND OF THE INVENTION

1. Field of the Invention

The present invention is in the field of electrochemical detection of organic compounds and more specifically concerns the electrochemical detection of nucleotides and nucleic acid polymers.

2. Background and Summary of the Invention

In the parent to the present application, which is incorporated herein by reference, the use of sinusoidal voltammetry for rapid detection of electroactive neurotransmitters was disclosed. The technique described using either lock-in amplifiers or fast Fourier transformation to detect these substances electrochemically employing miniature electrodes and extremely small sample volumes. These methods have now been extended to permit the detection of nucleic acids such as ribonucleic acid (RNA) and deoxyribonucleic acid (DNA).

The sensitive measurement of DNA and RNA is of primary importance due to the preeminent biological significance of these polymers as the primary genetic material and the primary transcriptional information carrier, respectively, of most living organisms. The knowledge of the structure of DNA, and its interactions with other biological compounds like proteins and other small molecular weight compounds might lead to advances in pharmacology, and also to the prevention of many diseases like cancer, sickle-cell anemia and cystic fibrosis. Traditionally, nucleic acids have been detected spectrophotometrically either directly (through UV absorbance of the purine and pyrimidine nucleotide bases) or indirectly through the use of various nucleic acid derivatives. Typical derivatives have included noncovalent labels such as intercalating dyes that operate through insertion into the nucleic acid helix or covalent labels that are directly attached to the nucleic acids which have been chemically derivatized. The added label may permit direct optical detection (i.e., the label is absorptive) or nonoptical detection (i.e., the label is radioactive). The added label may also permit binding of a secondary label such as an antibody which may itself be optically or radioactively labeled. It will be appreciated that derivatization-based methods are slow, complex and may result in sample loss or damage. On the other hand, direct optical detection is usually of insufficient sensitivity.

There is considerable need for extremely rapid, sensitive methods for nucleic acid detection. A primary use for such methods involves the growing demand for automated nucleic acid sequencing. Originally, nucleic acid sequencing involved digestion of the nucleic acids by specific nucleases (restriction enzymes) which cut the polymer adjacent to specific base sequences. The resulting fragments were accurately sized by electrophoresis on agarose gels and then detected through the use of intercalating fluorescent dyes or radioactive probes. The presence of fragments of specific molecular weights could then be used to deduce the sequence of bases in the nucleic acid polymer. To have sufficient material to be readily detected on the gels it was necessary to process relatively large amounts of nucleic acid with relatively large amounts of expensive restriction enzymes. A sensitive automated detection method could greatly speed the process and save money by reducing the need for labor, enzymes and other expensive consumables.

Electrochemical detection is particularly well suited for avoiding the problems of DNA analysis—particularly those caused by sample derivatization and the general problem of limited sample since it uses underivatized samples and can be miniaturized with ease—even to the point of working in nanoliter or even picoliter volumes—without sacrificing sensitivity. To date, most electrochemical detection protocols for nucleic acids have been based on the electroactivity of the nucleobases or the adsorption of single-stranded DNA (ssDNA) to complementary strands immobilized on a electrode surface (this also requires the use of an electroactive molecule that intercalates or otherwise associates with double-stranded DNA (dsDNA)).

Direct electrochemical detection of adenine and guanine bases is possible at mercury, gold, copper and carbon electrodes, where these bases can be oxidized at extremely positive potentials. Although these methods are quite sensitive for nucleic acid bases, high backgrounds and irreversible adsorption of larger molecules lead to poor sensitivity for this approach for the analysis of nucleosides, nucleotides and DNA. In particular, mercury, gold, and carbon surfaces were completely fouled by the adsorption of oligonucleotides and DNA strands. Several investigators subsequently exploited this adsorptive tendency of nucleic acid bases, oligonucleotides and DNA to obtain very sensitive electrochemical detection schemes. These schemes involved the adsorption of the nucleic acid onto the electrode surface in order to concentrate them, and then employed stripping voltammetric procedures to analyze the adsorbed analyte.

Indirect electrochemical detection utilizes electroactive moieties that can label dsDNA. Intercalators bind internally to the double stranded DNA formed at the surface of the electrode, allowing detection of the increased current at the electrode surface due to these species. Alternatively, electrostatic binding of cationic species can occur after intercalation or external binding of an electroactive molecule to DNA, where it can be monitored by electrochemistry of by electrogenerated chemiluminescence. All these methods, however, work on a batch process level, since they require the adsorption of nucleic acids and/or their components to the electrode surface for relatively long period of time (tens of seconds to 10–15 minutes). Therefore, they are not suitable for rapid flow-through detection schemes, such as those that can be coupled to separation methods like liquid chromatography and capillary electrophoresis.

Surprisingly, there have been no reports of the direct electrochemcial measurement of nucleotides or nucleic acids based on the oxidation of their ribose sugar moiety (deoxyribose in the case of DNA). Sugars can be detected at noble metal electrodes by employing pulsed amperometric detection or at electrocatalytic metal (e.g., nickel, lead, gold, copper and similar metals) electrodes by using DC detection. Since detection of sugars is accomplished via an electrocatalytic mechanism, it should also be possible to detect nucleotides via a similar mechanism. In particular, the use of a copper electrode minimizes the possibility of fouling of the electrode surface, since the Cu(II) layer is soluble in high pH buffer, and thus the oxidation of sugars and amines does not cause fouling of the copper surface since the surface is constantly washed off and renewed. Additionally, the potential at the electrode can be continuously cycled as conventionally done in most voltammetric measurements. Unfortunately, voltammetric techniques give poorer detection limits even compared to UV absorbance detection due to the high background charging currents observed when scanning the electrode surface rendering conventional voltammetric methods not very useful for nucleotide or nucleic acid analysis.

The parent to the instant application disclosed new scanning electrochemical methods which effectively decouple the background charging current from the Faradaic current in the frequency domain. This is accomplished by capitalizing on the inherent difference between charging and Faradaic currents. The background or charging currents are mostly linear, and therefore are present primarily at the fundamental excitation frequency. The Faradaic currents are essentially nonlinear at fast scan rates and thus have significant components even in the higher harmonics. By utilizing a sinusoidal excitation waveform, the charging current can be effectively isolated from the Faradaic current signal at higher harmonics, therefore sinusoidal voltammetry can be more sensitive than most traditional electrochemical methods.

The present invention employs a detection approach based on the electrocatalytic oxidation of the sugar backbone present on nucleotides and nucleic acids such as DNA. Electrocatalytic metal surfaces, especially copper surfaces, have been found to catalyze the oxidation of ribose (deoxyribose) sugars, without being fouled by the adsorption of the large DNA strands. This enables the detection of native, underivatized nucleotides, oligonucleotides and DNA strands. Adenine and cytosine, representing the two classes of nucleic acid bases, can be detected with nanomolar detection limits at a copper electrode under the preferred experimental conditions, where the sensitivity for adenine is somewhat higher than that for cytosine. Detection limits for purine-containing nucleotides (e.g., adenosine 5'-monophosphate (AMP), adenosine 5'-diphosphate (ADP), and adenosine 5'-triphosphate (ATP)) are on the order of 70–200 nM. These detection limits are achieved for native nucleotides and are over two orders of magnitude lower than those found with UV absorbance detection. Pyrimidine-based nucleotides could also be detected with high sensitivity due to the presence of the sugar backbone which is electroactive at the copper surface. Because this type of detector is not fouled by the nucleotides, it can be used for sensitive detection of analytes eluting continuously from either a chromatography column or an electrophoresis capillary.

In addition to nucleotides, entire nucleic acid molecules are readily detected. Both single stranded and double stranded DNA were detected with a detection limit in the picomolar concentration range (i.e., $10^{-12}$ moles/L). As the number of ribose sugar moieties increases with the chain length of a nucleic acid polymer, the sensitivity for detection also increases. This facilitates the detection of large DNA strands. Also, all previous detection strategies which are based on electroactivity of the bases face a severe decrease in signal for dsDNA as compared to ssDNA since the bases are on the inside of a double helix where their detection is sterically hindered by the surrounding sugars. In the present invention, the signal from a dsDNA is roughly twice that arising from ssDNA strand of the same length.

Sugars are oxidized at copper (at potentials>+0.4 Volts) due to the electrocatalytic mechanism involving the redox couple Cu(III)→Cu(II). Since nucleotides and DNA are large molecules which tend to irreversibly adsorb onto most electrodes, the potential applied to the electrode surface must be scanned through the region at which copper is oxidized. Unfortunately, most electrochemical methods which scan the applied potential do not have sensitivity comparable to DC detection schemes. However, sinusoidal voltammetry (previously disclosed as large amplitude AC voltammetry) is able to detect sugars at a copper surface with very high sensitivity and selectivity compared to existing electrochemical methods.

The electrochemical response can also be characterized in terms of the length of the oligonucleotide and the DNA strands. Frequency domain detection technique is used to detect oligonucleotides, and DNA under experimental conditions similar to those needed for the detection of simple sugars; however, a lower excitation frequency of 2 Hz is preferably used to account for the relatively slower kinetics (i.e., larger molecules) of nucleotides and nucleic acids as compared to those for much smaller mono- and disaccharides. Since nucleotides also contain amine moieties in the nucleobases, and these are also electroactive at a copper surface, some signal from the nucleotides can be contributed by these bases apart from that due to the sugar backbone. Thus, the nature of the nucleobase does change the observed signal both in magnitude and phase angle, and the frequency pattern can be used to differentiate different bases. Thus providing enhanced usefulness of the present invention in automated nucleic acid sequencers by allowing discrimination of base types.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1A:
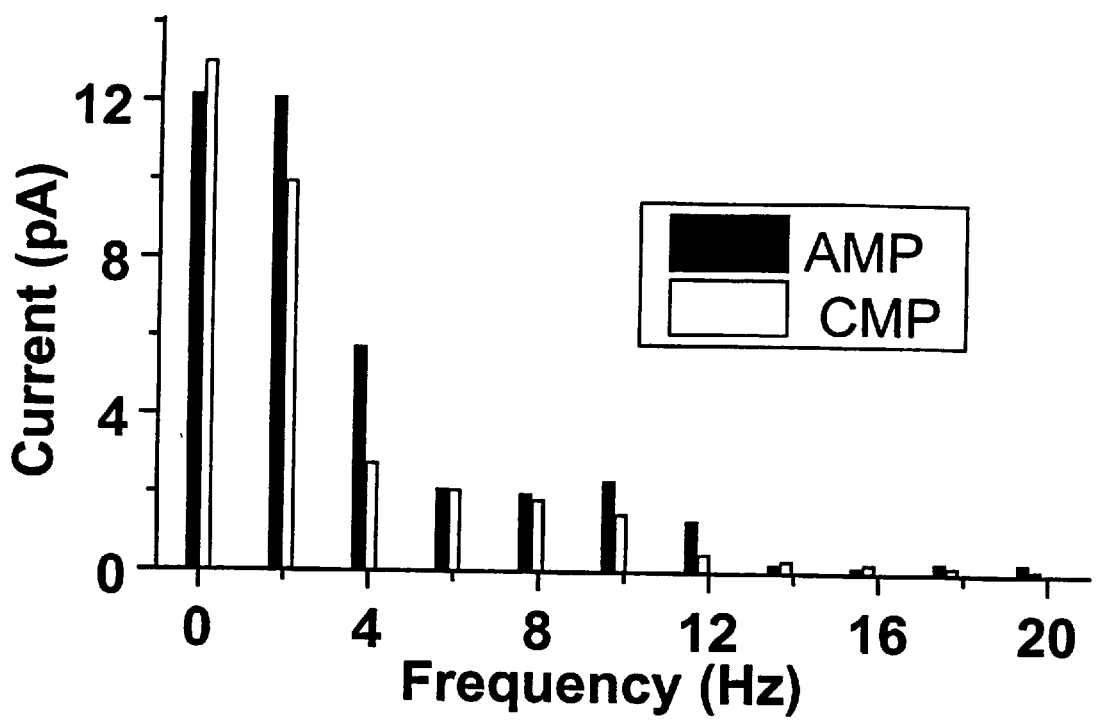
FIG. 1A shows background subtracted frequency spectra for AMP and CMP. Sample concentration: 100 $\mu$M each (A) AMP (■), CMP (□) at different harmonics. Signal spectra shown correspond to signal obtained at time (t)=95 seconds after the start of the 60 sec FIA injection; sinusoidal excitation with 2 Hz sine wave, 0.05–0.55 $V_{peak\ to\ peak}$ vs Ag/AgCl. with a running 0.1M NaOH electrolyte with a flow rate=0.5 mL/min.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a method for detecting nucleotides and nucleic acid strands by sinusoidal voltammetry on a copper electrode.

Experimental Methods

The present invention employs electrocatalytic metal electrodes—particularly copper microelectrodes—to detect nucleotides and nucleic acids. The fabrication of 20 $\mu$m Cu microelectrodes has been described elsewhere (Singhal et al., *Anal. Chem* 69:1662 (1997)). Prior to use, the electrodes are polished with a 1 $\mu$m diamond polish, followed by sonication in water. No electrochemical activation is performed in an effort to minimize the occurrence of background Faradaic processes at the electrode surface. The potential at the electrode is cycled under the experimental conditions for about an hour prior to the collection of data to achieve a stable background response.

The flow injection analysis (FIA) apparatus used has been described previously (Kristensen et al., *Anal. Chem.* 59:1752 (1987)) and includes a pneumatic actuator (Rheodyne, model 5701) controlled via a solenoid valve (Rheodyne kit, model 7163). The detection cell was designed to match the internal diameter of the FIA tubing (0.75 mm) to minimize diffusional broadening of the analyte as it was transported to the microelectrode. Finally, the flow rate (0.5 mL/min) was controlled by gravity flow by maintaining a height difference of 25 cm between the running electrolyte container and the flow cell. The volume of sample injected into the flow stream was determined by the flow rate and the length of the injection period. Typically, an injection time of 60 seconds was used, producing an injection volume of 500 $\mu$l. This injection protocol allowed the electrode to see the full concentration of the injected sample without dispersion or dilution, thereby giving a flat-top response.

Slow scan cyclic voltammetry and sinusoidal voltammetry were generally performed as described previously (Singhal et al.). Sinusoidal voltammetry was performed by digitally generating a 2 Hz sine wave (exactly 1.95 Hz, 0.05 V to 0.55 Volts vs. Ag/AgCl) with software provided by Axon Instruments (SineVolt; Axon Instruments Inc., Foster City, Calif.). This excitation waveform was filtered with a four-pole low pass filter having a 3 dB point at a frequency three times the fundamental frequency using a Cyberamp (Model 380, Axon Instruments Inc., Foster City, Calif.). The filtered excitation waveform was supplied to the Cu electrode through a three-electrode potentiostat (Geneclamp, Axon Instruments Inc., Foster City, Calif.). The current output of the potentiostat was filtered with the Cyberamp with a four pole low pass filter having a 3 dB point at 200 Hz (a frequency ten times higher than the highest frequency of interest), then by a second four-pole filter set at 40 Hz to further minimize noise contributions. The current was sampled digitally with a 12 bit A/D (1200A, Axon Instruments Inc., Foster City, Calif.) at a rate of 500 Hz using an 80486 IBM compatible personal computer. Leakage was avoided by sampling a wide bandwidth (over 10,000 points). Normally two sinusoidal cycles were obtained in a single scan, and 240 such scans were collected for one FIA measurement. Acquiring a large number of scans increases the resolution at the lower frequencies, while a longer sampling time minimizes artifacts due to convolution with the window function of the data.

Background subtraction was performed continuously as follows. A background signal was acquired digitally prior to each FIA experiment, then converted back into an analog signal which was subtracted from all subsequent current measurements prior to digitization of the instantaneous signal. This was done to minimize the low frequency components associated with background signal at the copper electrode, so as to increase the dynamic range for the measurement of the signal due to nucleotides and nucleic acids. The time domain data acquired in this manner was converted into the frequency domain with Fourier transform methods using commercial software (MATLAB 4.2.c.1, The Mathworks, Inc., Englewood Cliffs, N.J.).

The protocol for analyzing frequency spectra was the same as used by Singhal et al. Briefly, frequency spectra of the signal (only) was obtained simply by digital subtraction of a background vector from the instantaneous current vector. Time course data were obtained through the digital equivalent of lock-in amplification. Successive 512 point segments of the data were Fourier transformed sequentially into the frequency domain, generating the magnitude and phase information for each frequency element. Since all of the Faradaic information is contained within the harmonics of the excitation waveform, only these frequency elements were examined. Phase selectivity at each harmonic frequency was obtained by taking the projection of the instantaneous current at the phase angle of the background-subtractedsignal. Finally, the phase-resolved projections of each segment were low-pass filtered as a function of time. The time course information was generated after averaging several (e.g., ten) such projections together by using a moving average smoothing (essentially moving boxcar integration) as a low-pass filter.

Sinusoidal voltammetry uses a sine wave excitation which is used to elicit a current response at the electrode surface. The response obtained is converted into the frequency domain, and all the harmonics of the fundamental excitation are monitored, since these contain almost all of the current response obtained. The more nonlinear nature of the Faradaic current compared to the background charging current is used to sensitively discriminate the analyte signal over the background signal. The measurement at the higher harmonics is consequently much more sensitive than all time domain based electroanalytical methods.

Figure 1B:
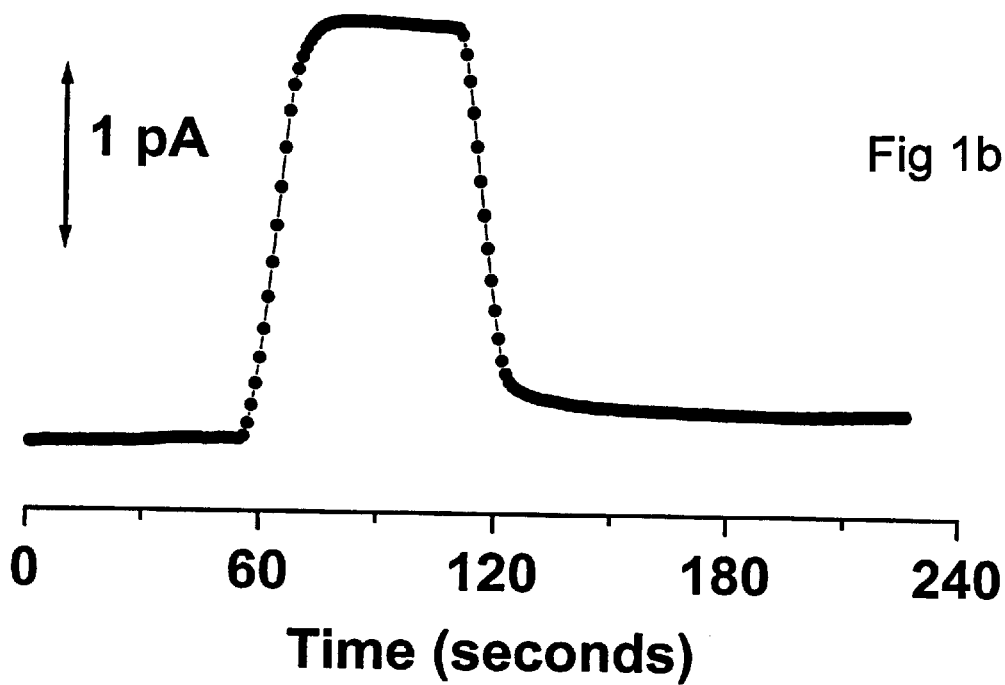
FIG. 1B shows the time course for the FIA injection at the fifth harmonic for 100 $\mu$M AMP for which the frequency spectra is shown above; the fifth harmonic was found the most sensitive for the detection of AMP; sinusoidal excitation with 2 Hz sine wave, 0.05–0.55 $V_{peak\ to\ peak}$ vs Ag/AgCl.. with a running 0.1M NaOH electrolyte with a flow rate=0.5 mL/min.

FIG. 1A shows the frequency spectrum of the electrochemical signal due to the two classes of nucleotides, namely purine-based adenosine 5' monophosphate (AMP) and pyrimidine-based cytosine 5' monophosphate (CMP). Purine bases are traditionally considered more electroactive at most surfaces, but at copper, it was found that pyrimidine-based cytosine also gave an appreciable signal in the frequency domain, albeit smaller than that due to adenine (data not shown). This could be possibly due to the amine present on the cytosine base which is electrocatalytically detected at the copper electrode. The adenine-containing nucleotide, AMP showed a detection limit in the nanomolar concentration range (FIG. 1B), as a result of the high electroactivity of adenine and also the presence of the sugar backbone. Even though cytosine base had a lower signal in the higher harmonics (due to its lower electroactivity on copper), CMP was still detected with high sensitivity (also in the nanomolar concentration range) with significant signal in the higher harmonics. This demonstrates that the current invention works for both purine and pyrimidine nucleotides.

Since DNA is simply a polynucleotide containing purine and pyrimidine bases, it is also possible to detect underivatized DNA using the present invention. The important feature in this scheme is that the signal is proportional to the strand length (even with dsDNA), because the electroactive sugars lie on the outer perimeter of the DNA strand and, thus, are available for detection at the electrocatalytic surface. This is in contrast to detection schemes at carbon and other surfaces which are entirely dependent on the electroactivity of the purine bases, which bases are shielded by the sugar and phosphate backbone present in a double helix for a dsDNA.

Figure 2A:
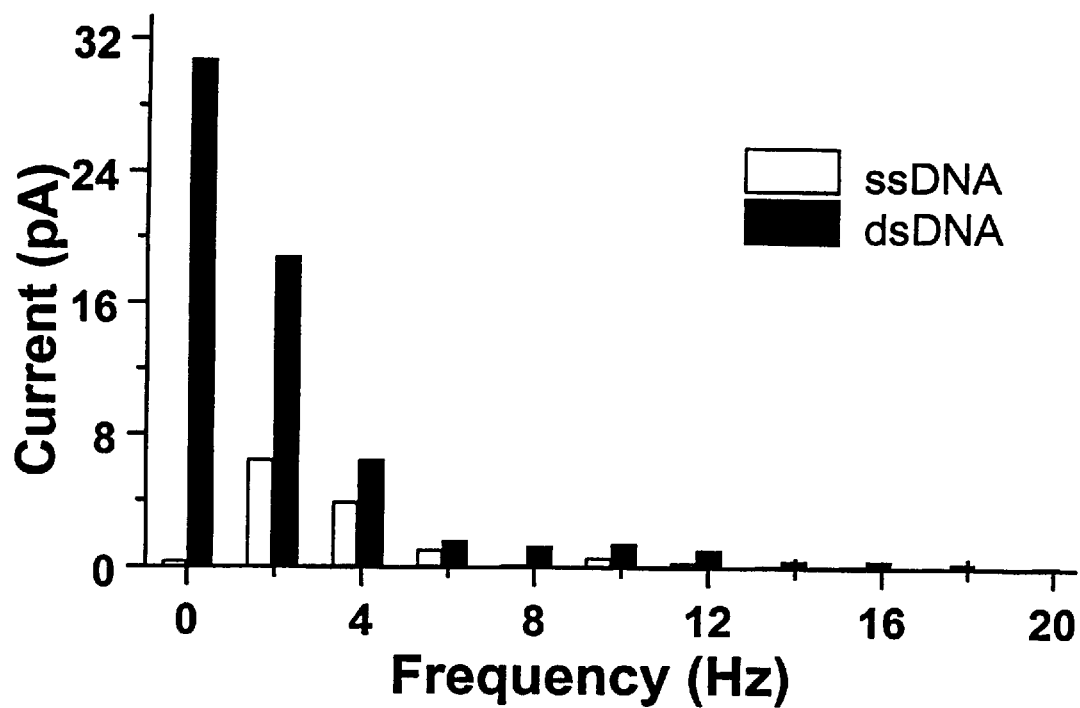
FIG. 2A shows background subtracted frequency spectra for ssDNA and dsDNA.; dsDNA was 9.5 kbp in length and ssDNA was obtained by denaturing a fraction of the dsDNA sample; sample concentration: 1 nM dsDNA (■), 2 nM ssDNA (□) showing frequency spectra at different harmonics at time (t)=95 seconds after start of the FIA injection; all other experimental conditions same as in FIG. 1.
Figure 2B:
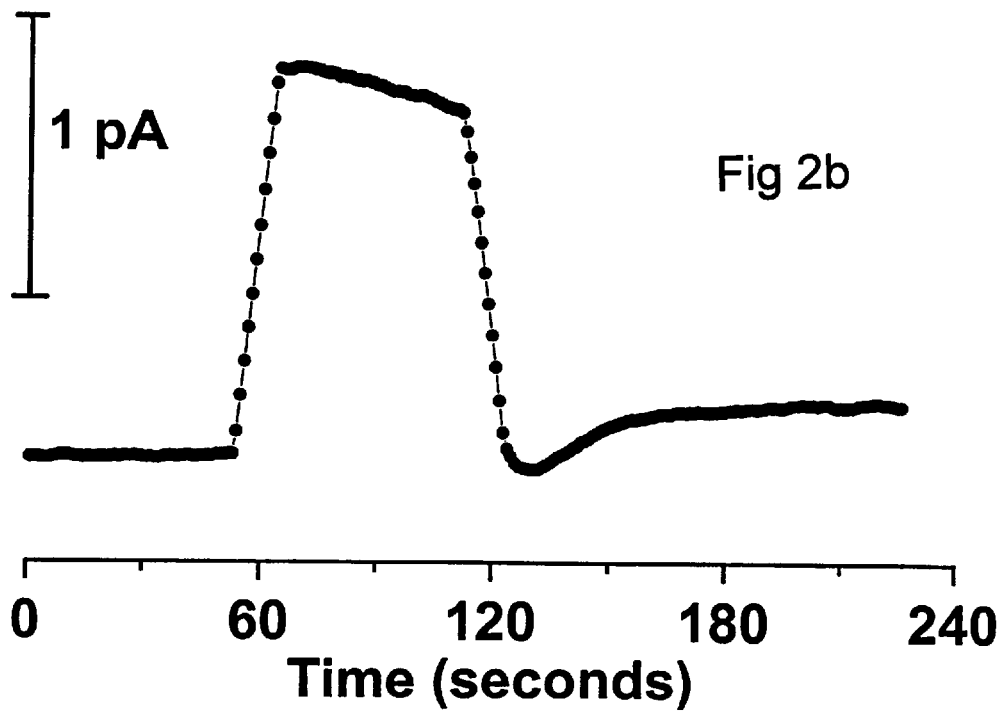
FIG. 2B shows the time course for the FIA injection at the sixth harmonic for 1 nM dsDNA for which the frequency spectra is shown in FIG. 2A; the sixth harmonic was found the most sensitive for the detection of dsDNA; all other experimental conditions same as in FIG. 1.

FIG. 2A shows the frequency spectra due to ssDNA and dsDNA. The signal from the dsDNA actually shows greater intensity than that of ssDNA because the dsDNA has more ribose sugar moieties available for detection. A similar trend in signal was noticed for the oligonucleotides examined, but the overall signals were smaller because these molecules contain a smaller number of sugar moieties. FIG. 2B shows the time course for the signal due to dsDNA at the sixth harmonic, which was found to be the best harmonic for detection of this analyte in terms of signal to noise ratio. The flow profile of the injection shows that there is no significant adsorption of the dsDNA at the copper surface. No loss was observed in electrode performance following repeated injections of dsDNA. This illustrates the reproducibility of the sensor for the detection of DNA. The detection limit (S/N= 3) for this dsDNA at the sixth harmonic is about three pM. These results corroborates the utility of a detection approach based on the electroactivity of sugars, as no decrease in sensitivity was encountered due to steric hindrances in a dsDNA relative to a ssDNA.

In summary, the detection of nucleotides, ssDNA and dsDNA can be achieved at a copper electrode surface using sinusoidal voltammetry. The present invention is based on the electrocatalytic oxidation of amine containing nucleobases, and the ribose sugar containing backbone of the nucleotides. Either purine or pyrimidine base-containing nucleotides or polymers can be readily detected because the ribose (deoxyribose) sugar moiety is universal to all nucleotides. The detection limits for both AMP and CMP are approximately on the order of 100–200 nM. Differences in the frequency domain in the response of these nucleotides can be used to differentiate the base type which differentiation is extremely useful for nucleic acid sequencers. Inspection of FIG. 1 shows that the frequency spectrum can provide a unique "fingerprint" for each nucleotide. That is, by comparing the signal (magnitude and phase angle) of each harmonic each nucleotide can be identified as to chemical type (i.e., as to purine versus pyrimidine and even as to specific base within these classes).

The sensitivity for ssDNA and dsDNA is even better due to the larger number of sugars present in these macromolecules compared to single nucleotides so that ssDNA and dsDNA were detected in the picomolar range. Sinusoidal voltammetry makes it possible to detect these big molecules with high sensitivity by preventing any fouling of the electrode surface, and by effectively decoupling the Faradaic signal from the large charging current background in the frequency domain. Detection of native, underivatized nucleotides and DNA is important for DNA sequencing applications involving exonuclease digestion products, and also as biosensors for detected DNA fragments unique to specific diseases.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

We claim:

1. A method for detecting nucleotides and nucleic acid polymers in a sample comprising the steps of:

contacting a surface of an electrocatalytic metal electrode with the sample dissolved in a high pH aqueous buffer;

applying a sinusoidal voltage having an amplitude and a fundamental frequency to the electrode, the amplitude being sufficient to elicit a redox reaction of at least one form of nucleotides and nucleic acid polymers in contact with the electrode;

measuring a current at the electrode, the current resulting from the elicited redox reaction;

producing a frequency spectrum of the measured current; and detecting the nucleotides and nucleic acid polymers by reference to a harmonic of the frequency spectrum greater than the fundamental frequency.

2. The method of claim 1, wherein the electrocatalytic metal is selected from the group consisting of copper, lead, gold and nickel.

3. The method of claim 1, wherein the fundamental frequency is between 1 and 5 Hz.

4. The method of claim 3, wherein the fundamental frequency is 2 Hz.

5. The method of claim 1, wherein signal at a fifth harmonic of the frequency spectrum is used to detect nucleotides.

6. The method of claim 1, wherein signal at a sixth harmonic of the frequency spectrum is used to detect nucleic acid polymers.

7. The method of claim 1, wherein the amplitude of the sinusoidal voltage ranges from about 0.05V to 0.55 V, measured against a silver/silver chloride electrode.

8. The method of claim 1 further comprising the step of comparing signal magnitude and phase angle at each harmonic of the frequency spectrum to identify a chemical type of each nucleotide detected.

9. A device for detecting nucleotides and nucleic acid polymers in a sample comprising:
- an electrocatalytic metal electrode;
- means for bringing a sample into contact with the electrode;
- means for applying a sinusoidal voltage having an amplitude and a fundamental frequency to the electrode, the amplitude being sufficient to elicit a redox reaction of at least one form of nucleotides and nucleic acid polymers at the electrode;
- means for measuring a current at the electrode, the current resulting from the elicited redox reaction;
- means for producing a frequency spectrum of the measured current; and
- means for analyzing signal at of least one harmonic of the frequency spectrum greater than the fundamental frequency to detect nucleotides and nucleic acid polymers.

10. The device of claim 9, wherein the fundamental frequency is between 1 and 5 Hz.

11. The device of claim 10, wherein the fundamental frequency is 2 Hz.

12. The device of claim 9, wherein the means for analyzing signal analyzes the signal at a fifth harmonic of the frequency spectrum to detect nucleotides.

13. The device of claim 9, wherein the means for analyzing signal analyzes the signal at a sixth harmonic of the frequency spectrum to detect nucleic acid polymers.

14. The device of claim 9, wherein the amplitude of the sinusoidal voltage ranges from about 0.05V to 0.55 V, measured against a silver/silver chloride electrode.

15. The device of claim 9, wherein the electrocatalytic metal is selected from the group consisting of copper, lead, gold and nickel.

16. The device of claim 9 further comprising means for comparing signal magnitude and phase angle at each harmonic of the frequency spectrum to identify a chemical type of each nucleotide detected.

17. A method for detecting nucleotides and nucleic acid polymers in a sample comprising the steps of:
- contacting a surface of a copper electrode with the sample dissolved in an aqueous buffer with a pH of more than 7.0;
- applying a sinusoidal voltage having an amplitude of from about 0.05 V to about 0.55 V, measured against a silver/silver chloride electrode, and a fundamental frequency of 2 Hz. to the copper electrode to elicit a redox reaction of at least one form of nucleotides and nucleic acid polymers at the copper electrode;
- measuring a current at the copper electrode, the current resulting from the elicited redox reaction;
- producing a frequency spectrum of the measured current; and
- detecting the nucleotides and nucleic acid polymers by reference to a harmonic of the frequency spectrum greater than the fundamental frequency.

18. The method of claim 17, wherein nucleotides are detected by reference to a fifth harmonic of the frequency spectrum.

19. The method of claim 17, wherein nucleic acid polymers are detected by reference to a sixth harmonic of the frequency spectrum.

20. The method of claim 17 further comprising the step of comparing signal magnitude and phase angle at each harmonic of the frequency spectrum to identify a chemical type of each nucleotide detected.

21. A device for detecting nucleotides and nucleic acid polymers in a sample comprising:
- a copper electrode;
- means for contacting the copper electrode with the sample dissolved in a high pH aqueous buffer;
- means for applying a sinusoidal voltage having an amplitude of from about 0.05 V to about 0.55 V, measured against a silver/silver chloride electrode, and a fundamental frequency of 2 Hz. to the copper electrode to elicit a redox reaction of nucleotides and nucleic acid polymers at the copper electrode;
- means for measuring a current at the copper electrode, the current resulting from the elicited redox reaction;
- means for producing a frequency spectrum of the measured current; and
- means for detecting the nucleotides and nucleic acid polymers by reference to a harmonic of the frequency spectrum greater than the fundamental frequency.

22. The device of claim 21, wherein the means for detecting the nucleotides detects the nucleotides by reference to a fifth harmonic of the frequency spectrum.

23. The device of claim 21, wherein the means for detecting the nucleic acid polymers detects the nucleotides by reference to a sixth harmonic of the frequency spectrum.

24. The device of claim 21 further comprising means for comparing signal magnitude and phase angle at each harmonic of the frequency spectrum to identify a chemical type of each nucleotide detected.

* * * * *